(12) United States Patent
Cho et al.

(10) Patent No.: US 8,447,546 B2
(45) Date of Patent: May 21, 2013

(54) MEASUREMENT OF FOURIER COEFFICIENTS USING INTEGRATING PHOTOMETRIC DETECTOR

(75) Inventors: Yong Jai Cho, Daejeon (KR); Won Chegal, Daejeon (KR); Hyun Mo Cho, Daejeon (KR)

(73) Assignee: Korea Research Institute of Standards and Science, Daejeon (KR)

( * ) Notice: Subject to any disclaimer, the term of this patent is extended or adjusted under 35 U.S.C. 154(b) by 274 days.

(21) Appl. No.: 12/840,849

(22) Filed: Jul. 21, 2010

(65) Prior Publication Data

US 2011/0077883 A1 Mar. 31, 2011

(30) Foreign Application Priority Data

Sep. 30, 2009 (KR) .................. 10-2009-0093444
Jan. 20, 2010 (KR) .................. 10-2010-0005358

(51) Int. Cl.
*G01R 13/00* (2006.01)

(52) U.S. Cl.
USPC ............................................. 702/66

(58) Field of Classification Search
USPC ............................................. 702/66
See application file for complete search history.

(56) References Cited

U.S. PATENT DOCUMENTS

| 7,064,829 | B2 * | 6/2006 | Li et al. | 356/369 |
| 7,450,232 | B2 * | 11/2008 | Li et al. | 356/369 |
| 2010/0116021 | A1 * | 5/2010 | O'Brien | 73/23.37 |

* cited by examiner

*Primary Examiner* — Aditya Bhat
(74) *Attorney, Agent, or Firm* — The Webb Law Firm

(57) ABSTRACT

Provided is a measurement method of Fourier coefficients using an integrating photometric detector, wherein, when measuring an exposure ($S_j$) with a predetermined time interval during a predetermined time period using an integrating photometric detector with respect to light of which amplitude varies with the time period, normalized Fourier coefficients ($\alpha'_{2n}$, $\beta'_{2n}$) for a waveform of an intensity of the light is determined by carrying out a discrete Fourier transform with respect to an equation for the measured exposure ($S_j$).

2 Claims, No Drawings

MEASUREMENT OF FOURIER COEFFICIENTS USING INTEGRATING PHOTOMETRIC DETECTOR

CROSS-REFERENCE(S) TO RELATED APPLICATIONS

The present invention claims priority of Korean Patent Application No. 10-2009-0093444, filed on Sep. 30, 2009 and Korean Patent Application No. 10-2010-0005358, filed on Jan. 20, 2010 which are incorporated herein by reference.

BACKGROUND OF THE INVENTION

1. Field of the Invention

The present invention relates to measurement of normalized Fourier coefficients for analyzing a waveform when measuring exposure in real time using an integrating photometric detector with respect to an intensity of an optical signal that varies periodically with time.

2. Description of Related Art

When measuring in real time an intensity of an optical signal that varies periodically with time (t) using an integrating photometric detector, Fourier coefficients are used to analyze the waveform. Assuming that there is no error in such measuring device, an intensity $I'(t)$ of light measured as an electric signal such as voltage or current by the photometric detector with respect to a specific wavelength can be expressed by the following equation consisting of a mean value $I_0'$ of the light intensity, normalized Fourier coefficients $\alpha'_{2n}$ and $\beta'_{2n}$, and a period (T):

$$I'(t) = I'_0 \left\{ 1 + \sum_{n=1}^{N} [\alpha'_{2n}\cos(4\pi nt/T) + \beta'_{2n}\sin(4\pi nt/T)] \right\}. \quad (1)$$

Where, 2N is a natural number that indicates a maximum degree of the normalized Fourier coefficients other than 0.

A representative example expressed by the equation (1) is a value of intensity of light measured with a photometric detector in a rotating optical element ellipsometer. The rotating optical element ellipsometer measures an intensity of light with a photometric detector in a state that an optical element such as a linear polarizer or a compensator rotates at a constant speed. In particular, an ellipsometer, a non-destructive and non-contacting realtime measuring device, is widely used to evaluate physical properties of nanofilms fabricated in various nanofilm processes such as a semiconductor device and a flat panel display.

In the case of rotating polarizer and rotating analyzer ellipsometers of various types of the rotating optical element ellipsometer, they have the same main elements: a light source, a polarizer (linear polarizer), a sample, an analyzer (linear polarizer), and a photometric detector, but measurement is carried out while only one of the polarizer and the analyzer rotates at a constant speed. This corresponds to a case that N is 1 in the equation (1), the intensity of the light measured by the photometric detector, since all other than the normalized Fourier coefficients of quadratic terms such as $\alpha'_2$ and $\beta'_2$ have the value of 0. In a case of a single rotating compensator ellipsometer, a compensator is added between the polarizer and the sample or between the sample and the analyzer of the aforementioned measuring device and this compensator alone rotates at a constant speed to carry out the measurement. This corresponds to a case that N is 2 in the equation (1), the intensity of the light measured by the photometric detector, since only the Fourier coefficients of quadratic and biquadratic terms such as $\alpha'_2$, $\beta'_2$, $\alpha'_4$ and $\beta'_4$ are not 0. In a case of a dual rotating compensator ellipsometer, the device consists of a light source, a polarizer, a compensator, a sample, a compensator, an analyzer and a photometric detector, and two compensators rotate at a relatively constant speed to carry out the measurement. In this case, N is 16 since the Fourier coefficients of effective terms of maximum degree in equation (1) are $\alpha'_{32}$ and $\beta'_{32}$.

In the ellipsometers, it is very important to obtain, more correctly, normalized Fourier coefficients $\alpha'_{2n}$ and $\beta'_{2n}$ from the waveform of the light intensity measured by the photometric detector like the equation (1). The realtime rotating optical element ellipsometer most widely used in recent generally employs a CCD detector array or a photodiode detector array as the photometric detector. These photometric detectors are called as an integrating photometric detector since they are in proportion to not only the light intensity but also an integration time $T_{int}$. This integrating photometric detector may carry out the measurement in a proper condition by properly reducing or increasing the integration time when the light amount is too much or insufficient upon the measurement, but the integration time upon the measurement should always be set to equal or larger than a minimum integration time of the relevant photometric detector. A value of the light amount, i.e. an exposure $S_j$, measured under a condition of measuring the light intensity, which varies periodically with time, M times with a constant interval T/M during the period T by the equation (1) using the aforementioned integrating photometric detector and matching the integration time correctly to the time interval, i.e. under a specific condition that $T_{int}=T/M$, is expressed as follows:

$$S_j = \int_{(j-1)T/M}^{jT/M} I'(t)dt, (j = 1, 2, 3, \ldots, M) \quad (2)$$

$$= \frac{I'_0 T}{M} + \sum_{n=1}^{N} \frac{I'_0 T}{2n\pi}\sin\left(\frac{2n\pi}{M}\right)$$

$$\left\{\alpha'_{2n}\cos\left[\frac{2n\pi(2j-1)}{M}\right] + \beta'_{2n}\sin\left[\frac{2n\pi(2j-1)}{M}\right]\right\}.$$

By solving simultaneous equations like the equation (2) with respect to the normalized Fourier coefficients, a formula of the normalized Fourier coefficients $\alpha'_{2n}$ and $\beta'_{2n}$ expressed by the exposure $S_j$ is obtained and this is called as the Hadamard transform. The equation (2) has been used as a representative method to be able to obtain the Fourier coefficients of the equation (1) in a case of using the integrating photometric detector in the rotating optical element ellipsometer. However, since in an actual integrating photometric detector, the photometric detector does not response during the time of reading out the light amount accumulated in each pixel during the integration time and initializing the status, i.e. read time $T_r$, the exposure of the equation (2) was corrected, in consideration of this fact, as follows:

$$S_j = \int_{(j-1)T/M+T_r}^{jT/M} I'(t)dt, (j = 1, 2, 3, \ldots, M), \quad (3)$$

and an equation obtained by the first-order approximation to $T_r$ is used on the assumption that the read time $T_r$ is very shorter than the measuring time interval T/M.

In the case of a conventional rotating polarizer or analyzer ellipsometer using the Hadamard transform, in the equation (1), T is a period of mechanical turn of a polarizer or analyzer and N is 1 as already described above. Also, although a minimum value of the measurement number M during the period T is 6, the measurement number M is increased to 8 since it is required to additionally measure $\beta'_4$ so as to found whether the system is normal or not. At this time, since the values of the exposure measured at each section are symmetric with respect to T/2 period, four unknown coefficients $I'_0$, $\alpha'_2$, $\beta'_2$ and $\beta'_4$ can be obtained from four simultaneous equations consisting of only $S_1$, $S_2$, $S_3$ and $S_4$ measured in the first half.

Meanwhile, in the case of a conventional single rotating compensator ellipsometer using the Hadamard transform, T is a period of mechanical turn of a compensator and N is 2. Also, although a minimum value of the measurement number M during the period T is 10, the measurement number M is increased to 16 since it is required to additionally measure $\beta'_8$ so as to found whether the system is normal or not. Like the previous case, a value of the simultaneous equation was used to obtain six unknown coefficients $I'_0$, $\alpha'_2$, $\beta'_2$, $\alpha'_4$, $\beta'_4$ and $\beta'_8$ from the measured values of $S_j$ (j=1, 2, 3, . . . , 8) in consideration of the symmetry of the measured values of the exposure.

Finally, in the case of a conventional dual rotating compensator ellipsometer using the Hadamard transform, 36 unknown coefficients were obtained in a very complex form by solving 36 simultaneous equations.

In the conventional rotating optical element ellipsometer using the Hadamard transform, the maximum degree 2N of the Fourier coefficients other than 0 is determined different according to the kind of the ellipsometer, there was used a complex equation for obtaining mean value $I'_0$ of the light intensity and normalized Fourier coefficients $\alpha'_{2n}$ and $\beta'_{2n}$ from the value $S_j$ of the exposure measurement by solving the simultaneous equation obtained by substituting the equation (1) into equation (2), and finally an error of the read time was corrected using the first-order approximation equation with respect to read time obtained from the equation (3).

With development of manufacturing technique of the integrating photometric detector, the read time and the minimum integration time have been reduced to 1 ms or less and a measurement sensitivity has been notably improved. Since it is possible to reduce the measurement time to several ms for the faster measurement, ratio of the read time to the measurement time interval is gradually increased. Therefore, a correction method more accurate than the conventional primary approximation to the read time is required for accurate measurement. Also, when using the conventional Hadamard transform, since sum of the read time and the integration time should be set to exactly accord with the measurement time interval, the light amount easily reaches to a saturation state within the short integration time when the light intensity is too high and thus some of the light beam should be shielded by using additional optical elements such as an iris diaphragm and a neutral density filter (ND filter).

SUMMARY OF THE INVENTION

To improve problems, such as complexity of equation, approximation correction to the read time and limited variation in the integration time, of the conventional method for obtaining Fourier coefficients by analyzing a waveform when measuring exposure in realtime using an integrating photometric detector with respect to an intensity of an optical signal that varies periodically with time, an embodiment of the present invention is directed to providing an equation for measuring Fourier coefficients which can wholly correct exposure measurement to arbitrary integration time and read time and reduce a minimum number of measurement as compared to prior technique, and is relatively very simple.

To achieve the object of the present invention, the present invention provides a measurement method of Fourier coefficients using an integrating photometric detector, wherein, when measuring an exposure ($S_j$) with a predetermined time interval during a predetermined time period using an integrating photometric detector with respect to light of which amplitude varies with the time period, normalized Fourier coefficients ($\alpha'_{2n}$, $\beta'_{2n}$) for a waveform of an intensity of the light is determined by carrying out a discrete Fourier transform with respect to an equation for the measured exposure ($S_j$).

Preferably, the equation for the measured exposure ($S_j$) is as follows:

$$S_j = \int_{(j-1)T/M+T_r}^{(j-1)T/M+T_r+T_{int}} I'(t)dt, \; (j=1, 2, 3, \ldots, M),$$

and the normalized Fourier coefficients ($\alpha'_{2n}$, $\beta'_{2n}$) for the waveform of the light intensity are respectively as follows:

$$\alpha'_{2n} = \xi_{2n}\csc(\xi_{2n})\left\{a_{2n}\cos\left[\xi_{2n}\left(1+\frac{2T_r}{T_{int}}\right)\right] - b_{2n}\sin\left[\xi_{2n}\left(1+\frac{2T_r}{T_{int}}\right)\right]\right\},$$

$$\beta'_{2n} = \xi_{2n}\csc(\xi_{2n})\left\{a_{2n}\sin\left[\xi_{2n}\left(1+\frac{2T_r}{T_{int}}\right)\right] + b_{2n}\cos\left[\xi_{2n}\left(1+\frac{2T_r}{T_{int}}\right)\right]\right\},$$

where T: period, M: number of measuring the exposure with the predetermined time interval during the period T, $T_r$: a read time, $T_{int}$: a integration time, $$I'(t) = I'_0\left\{1 + \sum_{n=1}^{N}[\alpha'_{2n}\cos(4\pi nt/T) + \beta'_{2n}\sin(4\pi nt/T)]\right\},$$

I'(t): light intensity, $I'_0$: mean value of the light intensity, $\alpha'_{2n}$ and $\beta'_{2n}$: normalized Fourier coefficients, 2N: natural number that indicates a maximum degree of the normalized Fourier coefficients other than 0, $\xi_n = n\pi T_{int}/T$, $$a_{2n} = 2/(Md_0)\sum_{j=1}^{M}S_j\cos[4n\pi(j-1)/M],$$

$$b_{2n} = 2/(Md_0)\sum_{j=1}^{M}S_j\sin[4n\pi(j-1)/M], \; d_0 = 1/(M)\sum_{j=1}^{M}S_j.$$

As described above, the present invention provides a measurement method of Fourier coefficients using an integrating photometric detector, which is wholly corrected to arbitrary integration time and read time, can reduce a number of measurement by about 2 times when applied to a rotating optical element ellipsometer and is relatively very simple, as compared to the conventional method for obtaining Fourier coefficients by analyzing a waveform when measuring exposure in realtime using an integrating photometric detector with respect to an intensity of an optical signal that varies periodically with time.

When applied to a rotating optical element ellipsometer, the present invention has advantages that it is possible to carries out the measurement under an optimum condition and measure more faster by controlling the integration time arbitrarily with a light intensity and thus productivity is improved when utilized in industries, and it is possible to carry out the measurement more accurately than the prior technique.

DESCRIPTION OF SPECIFIC EMBODIMENTS

The advantages, features and aspects of the invention will become apparent from the following description of the embodiments.

To solve the problems of the prior techniques as described above, first, the equation (3) for an exposure measured using an integrating photometric detector was corrected with respect to a specific read time $T_r$ and an arbitrary integration time $T_{int}$ as follows:

$$S_j = \int_{(j-1)T/M+T_r}^{(j-1)T/M+T_r+T_{int}} I'(t)\,dt, \quad (j = 1, 2, 3, \ldots, M). \tag{4}$$

By substituting the equation (1) into the equation (4) and carrying out a simple calculation, a resultant equation for the exposure $S_j$ is obtained, and a discrete Fourier transform to a term of an arbitrary degree is used thereto to obtain normalized Fourier coefficients for the term of the corresponding degree.

The substitution of the equation (1) into the equation (4) results in an exposure measurement equation corrected with respect to the read time and the integration time such as:

$$S_j = I'_0 T_{int} + \sum_{n=1}^{N} \frac{I'_0 T}{2n\pi} \sin\left(\frac{2n\pi T_{int}}{T}\right) \tag{5}$$
$$\left(\cos\left[\frac{4n\pi(j-1)}{M}\right]\right)\left\{\alpha'_{2n}\cos\left[\frac{2n\pi(T_{int}+2T_r)}{T}\right] + \beta'_{2n}\sin\left[\frac{2n\pi(T_{int}+2T_r)}{T}\right]\right\} - \sin\left[\frac{4n\pi(j-1)}{M}\right]$$
$$\left\{\alpha'_{2n}\sin\left[\frac{2n\pi(T_{int}+2T_r)}{T}\right] - \beta'_{2n}\cos\left[\frac{2n\pi(T_{int}+2T_r)}{T}\right]\right\}\right).$$

In particular, when $T_{int}=T/M$, $T_r=0$, the equation (5) agrees with the prior equation (2). To obtain unknown coefficients, orthogonality of trigonometrical function such as the following equations (6) and (7), which are valid under a specific condition for the number M of measuring the exposure with a predetermined time interval during one period T, is used, $$\frac{2}{M}\sum_{j=1}^{M}\cos\left[\frac{4n\pi(j-1)}{M}\right]\cos\left[\frac{4m\pi(j-1)}{M}\right] = \delta_{n,m}, \tag{6}$$

$$\frac{2}{M}\sum_{j=1}^{M}\sin\left[\frac{4n\pi(j-1)}{M}\right]\sin\left[\frac{4m\pi(j-1)}{M}\right] = \delta_{n,m}, \tag{7}$$

and, this is applied to the discrete Fourier transform for the exposure as follows:

$$d_0 = \frac{1}{M}\sum_{j=1}^{M} S_j = I'_0 T_{int}, \tag{8}$$

$$a_{2n} = \frac{2}{Md_0}\sum_{j=1}^{M} S_j \cos\left[\frac{4n\pi(j-1)}{M}\right] \tag{9}$$
$$= \frac{1}{\xi_{2n}}\sin(\xi_{2n})\left\{\alpha'_{2n}\cos\left[\xi_{2n}\left(1+\frac{2T_r}{T_{int}}\right)\right] + \beta'_{2n}\sin\left[\xi_{2n}\left(1+\frac{2T_r}{T_{int}}\right)\right]\right\},$$

$$b_{2n} = \frac{2}{Md_0}\sum_{j=1}^{M} S_j \sin\left[\frac{4n\pi(j-1)}{M}\right] \tag{10}$$
$$= \frac{1}{\xi_{2n}}\sin(\xi_{2n})\left\{-\alpha'_{2n}\sin\left[\xi_{2n}\left(1+\frac{2T_r}{T_{int}}\right)\right] + \beta'_{2n}\cos\left[\xi_{2n}\left(1+\frac{2T_r}{T_{int}}\right)\right]\right\},$$

where $\xi_n = n\pi T_{int}/T$. By solving the simultaneous equations of the equations (9) and (10), normalized Fourier coefficients for an arbitrary degree $2n$ of the equation (1) are obtained as follows:

$$\alpha'_{2n} = \xi_{2n}\csc(\xi_{2n})\left\{a_{2n}\cos\left[\xi_{2n}\left(1+\frac{2T_r}{T_{int}}\right)\right] - b_{2n}\sin\left[\xi_{2n}\left(1+\frac{2T_r}{T_{int}}\right)\right]\right\}, \tag{11}$$

$$\beta'_{2n} = \xi_{2n}\csc(\xi_{2n})\left\{a_{2n}\sin\left[\xi_{2n}\left(1+\frac{2T_r}{T_{int}}\right)\right] + b_{2n}\cos\left[\xi_{2n}\left(1+\frac{2T_r}{T_{int}}\right)\right]\right\}, \tag{12}$$

From the exposure $S_j$ measured with a regular time interval with respect to an arbitrary integration time, $d_0$, $a_{2n}$ and $b_{2n}$ of equations (8) to (10) are calculated, and these values are substituted into the equations (11) and (12) to thereby obtain the values of the normalized Fourier coefficients $\alpha'_{2n}$ and $\beta'_{2n}$ in which the error of the read time is wholly corrected.

When applying the present invention to a rotating polarizer or analyzer ellipsometer, in equation (1), T is a period of mechanical turn of the polarizer or analyzer, and N becomes 1 sine the normalized Fourier coefficients of terms of higher degree other than $\alpha'_2$ and $\beta'_2$ have the value of 0. Therefore, the light intensity measured for a certain wave length is given as follows:

$$I'(t) = I'_0[1 + \alpha'_2 \cos(4\pi t/T) + \beta'_2 \sin(4\pi t/T)]. \tag{13}$$

By using the equations (11) and (12), TTL pulse is generated one by one in an optical encoder when the minimum value of the measurement number M is 5 and an azimuth value of the rotating device provided with the polarizer or the analyzer is 0°, 72°, 144°, 216° and 288°, respectively, and these signals are transmitted as external trigger signals of the photometric detector to measure the values of the exposure $S_1$, $S_2$, $S_3$, $S_4$ and $S_5$, respectively. Therefore, by substituting n=1, 2 and M=5 into the equations (8) to (10), values of $d_0$, $a_2$, $b_2$, $a_4$ and $b_4$ are calculated as follows from the values of $S_1$, $S_2$, $S_3$, $S_4$ and $S_5$ measured by the integrating photometric detector.

$$d_0 = \frac{1}{5}(S_1 + S_2 + S_3 + S_4 + S_5), \tag{14}$$

-continued $$a_2 = \frac{2}{S_1 + S_2 + S_3 + S_4 + S_5}\left[S_1 + S_2\cos\left(\frac{4\pi}{5}\right) + \right.$$
$$\left. S_3\cos\left(\frac{8\pi}{5}\right) + S_4\cos\left(\frac{12\pi}{5}\right) + \right.$$
$$\left. S_5\cos\left(\frac{16\pi}{5}\right)\right], \quad (15)$$

$$b_2 = \frac{2}{S_1 + S_2 + S_3 + S_4 + S_5}\left[S_2\sin\left(\frac{4\pi}{5}\right) + S_3\sin\left(\frac{8\pi}{5}\right) + \right.$$
$$\left. S_4\sin\left(\frac{12\pi}{5}\right) + S_5\sin\left(\frac{16\pi}{5}\right)\right], \quad (16)$$

$$a_4 = \frac{2}{S_1 + S_2 + S_3 + S_4 + S_5}\left[S_1 + S_2\cos\left(\frac{8\pi}{5}\right) + S_3\cos\left(\frac{16\pi}{5}\right) + \right.$$
$$\left. S_4\cos\left(\frac{24\pi}{5}\right) + S_5\cos\left(\frac{32\pi}{5}\right)\right], \quad (17)$$

$$b_4 = \frac{2}{S_1 + S_2 + S_3 + S_4 + S_5}\left[S_2\sin\left(\frac{8\pi}{5}\right) + S_3\sin\left(\frac{16\pi}{5}\right) + \right.$$
$$\left. S_4\sin\left(\frac{24\pi}{5}\right) + S_5\sin\left(\frac{32\pi}{5}\right)\right]. \quad (18)$$

By substituting the values obtained as such into the equations (8), (11) and (12), following equations are obtained.

$$I'_0 = \frac{d_0}{T_{int}}, \quad (19)$$

$$\alpha'_2 = \frac{2\pi T_{int}}{T}\csc\left(\frac{2\pi T_{int}}{T}\right)\left\{a_2\cos\left[\frac{2\pi(T_{int} + 2T_r)}{T}\right] - b_2\sin\left[\frac{2\pi(T_{int} + 2T_r)}{T}\right]\right\}, \quad (20)$$

$$\beta'_2 = \frac{2\pi T_{int}}{T}\csc\left(\frac{2\pi T_{int}}{T}\right)\left\{a_2\sin\left[\frac{2\pi(T_{int} + 2T_r)}{T}\right] + b_2\cos\left[\frac{2\pi(T_{int} + 2T_r)}{T}\right]\right\}, \quad (21)$$

$$\beta'_4 = \frac{4\pi T_{int}}{T}\csc\left(\frac{4\pi T_{int}}{T}\right)\left\{a_4\sin\left[\frac{4\pi(T_{int} + 2T_r)}{T}\right] + b_4\cos\left[\frac{4\pi(T_{int} + 2T_r)}{T}\right]\right\}. \quad (22)$$

Herein, $\beta'_4$ is used to examine system state since it should be 0, as can be seen from the equation (13), when there is no system error, and $\alpha'_2$ and $\beta'_2$ are used to obtain physical properties of a sample by analyzing them using an optical model. Although the value of the number M of the measurement during the mechanical turn period T is 8 in the prior art of the rotating polarizer or analyzer ellipsometer, the measurement speed can be improved to 1.6 times under the same condition since the value of M can be reduced to 5 as described above in the present invention.

When applying the present invention to a single rotating compensator ellipsometer, T is a period of mechanical turn of the compensator, N is 2, and the minimum value of the measurement number M during the period T becomes 7 to measure the values of $S_j$ (j=1, ..., 7), and the values of $d_0$, $a_j$ (j=2, 4, 6) and $b_j$ (j=2, 4, 6) are calculated from equations (8) to (10) and these values are substituted into the equations (8), (11) and (12) to calculate the values of $I'_0$, $\alpha'_2$, $\beta'_2$, $\alpha'_4$, $\beta'_4$, $\alpha'_6$ and $\beta'_6$. Herein, $\alpha'_2$, $\beta'_2$, $\alpha'_4$ and $\beta'_4$ are used to calculate the physical properties of a sample, and $\alpha'_6$ and $\beta'_6$ are used to examine whether the system is normal or not. Under the same condition, in the prior technique, the measurement number M was set to 16 and 6 values of the simultaneous equations were used to obtain 6 unknown coefficients. Therefore, when applying the present invention to a single rotating compensator ellipsometer, it is possible to carry out the measurement 2.3 times faster since the measurement number less than that of the prior technique is used.

Since the measurement number can be 37 by application of the present invention while the minimum value of M is 72 in a dual rotating compensator ellipsometer of which the term of the maximum degree of the normalized coefficients to be measured in the prior technique, the measurement speed of the present invention is 1.9 times faster than that of the prior technique.

A representative application of the present invention is to measure normalized Fourier coefficients in a rotating optical element ellipsometer which is widely used as a measurement device for semiconductor and display industries.

While the present invention has been described with respect to the specific embodiments, it will be apparent to those skilled in the art that various changes and modifications may be made without departing from the spirit and scope of the invention as defined in the following claims.

What is claimed is:

1. A measurement method of Fourier coefficients using an integrating photometric detector, comprising:
   measuring a number of exposures ($S_j$) of light with a predetermined integration time during a predetermined time period using the integrating photometric detector; and
   determining Fourier coefficients for a waveform of an intensity of the light by carrying out a discrete Fourier transform with respect to the number of measured exposures ($S_j$) wherein the number of exposures ($S_j$) are measured using the integrating photometric detector with a read time ($T_r$) as follows:

$$S_j = \int_{(j-1)T/M+T_r}^{(j-1)T/M+T_r+T_{int}} I'(t)\,dt, \quad (j = 1, 2, 3, \Lambda, M),$$

with a predetermined integration time ($T_{int}$) for a time period (T) and then, from the number of measured exposures ($S_j$), the normalized Fourier coefficients ($\alpha'_{2n}, \beta'_{2n}$) for the waveform of the light intensity are determined respectively as follows:

$$\alpha'_{2n} = \xi_{2n}\csc(\xi_{2n})\left\{a_{2n}\cos\left[\xi_{2n}\left(1 + \frac{2T_r}{T_{int}}\right)\right] - b_{2n}\sin\left[\xi_{2n}\left(1 + \frac{2T_r}{T_{int}}\right)\right]\right\},$$

$$\beta'_{2n} = \xi_{2n}\csc(\xi_{2n})\left\{a_{2n}\sin\left[\xi_{2n}\left(1 + \frac{2T_r}{T_{int}}\right)\right] + b_{2n}\cos\left[\xi_{2n}\left(1 + \frac{2T_r}{T_{int}}\right)\right]\right\},$$

{T: period,
M: number of measuring the exposure with the predetermined time interval during the period T,
$T_r$: read time,
$T_{int}$: integration time, $$I'(t) = I'_0\left\{1 + \sum_{n=1}^{N}[\alpha'_{2n}\cos(4\pi nt/T) + \beta'_{2n}\sin(4\pi nt/T)]\right\},$$

I'(t): light intensity,
$I'^0$: mean value of the light intensity, $\alpha'_{2n}$ and $\beta'_{2n}$: normalized Fourier coefficients,
2N : natural number that indicates the highest order of the normalized Fourier coefficients other than 0, $$\xi_n = \frac{n\pi T_{int}}{T},$$

$$a_{2n} = \frac{2}{Md_0}\sum_{j=1}^{M} S_j \cos\left[\frac{4n\pi(j-1)}{M}\right],$$

$$b_{2n} = \frac{2}{Md_0}\sum_{j=1}^{M} S_j \sin\left[\frac{4n\pi(j-1)}{M}\right],$$

$$d_0 = \frac{1}{M}\sum_{j=1}^{M} S_j \bigg\}.$$

2. A method for measuring Fourier coefficients using an integrating photometric detector, comprising: determining, using the integrating photometric detector, normalized Fourier coefficients ($\alpha'_{2n}, \beta'_{2n}$) for a waveform of an intensity of a light by carrying out a discrete Fourier transform with respect to multiple measured exposures ($S_j$) of the light with a predetermined integration time during a predetermined time period, wherein the normalized Fourier coefficients ($\alpha'_{2n}, \beta'_{2n}$) are determined when the exposures ($S_j$) are measured during a predetermined time period, wherein an amplitude of the light varies with the time period, and wherein the multiple measured exposures ($S_j$) are as follows:

$$S_j = \int_{(j-1)T/M+T_r}^{(j-1)T/M+T_r+T_{int}} I'(t)\,dt, \ (j=1, 2, 3, \Lambda, M),$$

and the normalized Fourier coefficients ($\alpha'_{2n}, \beta'_{2n}$) for the waveform of the light intensity are determined respectively as follows:

$$\alpha'_{2n} = \xi_{2n}\csc(\xi_{2n})\left\{a_{2n}\cos\left[\xi_{2n}\left(1+\frac{2T_r}{T_{int}}\right)\right] - b_{2n}\sin\left[\xi_{2n}\left(1+\frac{2T_r}{T_{int}}\right)\right]\right\},$$

$$\beta'_{2n} = \xi_{2n}\csc(\xi_{2n})\left\{a_{2n}\sin\left[\xi_{2n}\left(1+\frac{2T_r}{T_{int}}\right)\right] + b_{2n}\cos\left[\xi_{2n}\left(1+\frac{2T_r}{T_{int}}\right)\right]\right\},$$

{T: period,
M: number of measuring the exposure with the predetermined time interval during the period T,
$T_r$: read time,
$T_{int}$: integration time, $$I'(t) = I'_0\left\{1 + \sum_{n=1}^{N}[\alpha'_{2n}\cos(4\pi nt/T) + \beta'_{2n}\sin(4\pi nt/T)]\right\},$$

I'(t): light intensity,
I'$_0$: mean value of the light intensity,
$\alpha'_{2n}$ and $\beta'_{2n}$: normalized Fourier coefficients,
2N : natural number that indicates the highest order of the normalized Fourier coefficients other than 0, $$\xi_n = \frac{n\pi T_{int}}{T},$$

$$a_{2n} = \frac{2}{Md_0}\sum_{j=1}^{M} S_j \cos\left[\frac{4n\pi(j-1)}{M}\right],$$

$$b_{2n} = \frac{2}{Md_0}\sum_{j=1}^{M} S_j \sin\left[\frac{4n\pi(j-1)}{M}\right],$$

$$d_0 = \frac{1}{M}\sum_{j=1}^{M} S_j \bigg\}.$$

* * * * *

UNITED STATES PATENT AND TRADEMARK OFFICE
CERTIFICATE OF CORRECTION

PATENT NO. : 8,447,546 B2
APPLICATION NO. : 12/840849
DATED : May 21, 2013
INVENTOR(S) : Yong Jai Cho et al.

It is certified that error appears in the above-identified patent and that said Letters Patent is hereby corrected as shown below:

In the Claims

Column 8, Line 67, Claim 1, delete "$I'^0$" and insert -- $I'_0$ --

Signed and Sealed this
First Day of October, 2013

Teresa Stanek Rea
*Deputy Director of the United States Patent and Trademark Office*